(12) United States Patent
Forster et al.

(10) Patent No.: US 12,377,065 B2
(45) Date of Patent: Aug. 5, 2025

(54) COMPOSITIONS FOR TREATMENT OF SUBSTANCE USE DISORDER

(71) Applicant: UNIVERSITY OF NORTH TEXAS HEALTH SCIENCE CENTER, Fort Worth, TX (US)

(72) Inventors: Michael J. Forster, Fort Worth, TX (US); Ritu A. Shetty, Fort Worth, TX (US); Jacques Nguyen, Fort Worth, TX (US); Liang-Jun Yan, Fort Worth, TX (US)

(73) Assignee: UNIVERSITY OF NORTH TEXAS HEALTH SCIENCE CENTER, Ft. Worth, TX (US)

( * ) Notice: Subject to any disclaimer, the term of this patent is extended or adjusted under 35 U.S.C. 154(b) by 847 days.

(21) Appl. No.: 17/628,138

(22) PCT Filed: Jul. 17, 2020

(86) PCT No.: PCT/US2020/070291
§ 371 (c)(1),
(2) Date: Jan. 18, 2022

(87) PCT Pub. No.: WO2021/016637
PCT Pub. Date: Jan. 28, 2021

(65) Prior Publication Data
US 2022/0233479 A1 Jul. 28, 2022

Related U.S. Application Data

(60) Provisional application No. 62/876,532, filed on Jul. 19, 2019.

(51) Int. Cl.
*A61K 31/17* (2006.01)
*A61K 45/06* (2006.01)

(52) U.S. Cl.
CPC .............. *A61K 31/17* (2013.01); *A61K 45/06* (2013.01)

(58) Field of Classification Search
CPC ................................ A61K 31/17; A61K 45/06
See application file for complete search history.

(56) References Cited

U.S. PATENT DOCUMENTS

2016/0106808 A1  4/2016  Charney et al.

OTHER PUBLICATIONS

ASHP Handbook on Injectable Drugs, Toissel, 4$^{th}$ ed., pp. 622-630 (1986).
Badiani "Substance-specific environmental influences on drug use and drug preference in animals and humans" 2013.
Dietrich et al., "Acute or repeated cocaine administration generates reactive oxyen species and induces antioxidant enzyme activity in dopaminergic rat brain structures" 2005.
Kun-Lun Huang et al., "Free radicals mediate amphetamine-induced acute pulmonary edema in isolated rat lung", Life Science vol. 71. No. 11, Aug. 1, 2002, pp. 1237-1244.
Labib et al., "Endotoxin Potentiates Cocaine-Mediated Hepatotoxicity by Nitric Oxide and Reactive Oxygen Species" 2003.
Moritz et al., Cardiovascular Research 59 "Role of reactive oxygen species in cocaine-induced cardiac dysfunction" pp. 834-843, 2003.
Moussawi et al., Nature Neuroscience 12, 182-189 "N-Acetylcysteine reverses cocaine-induced metaplasticity" 2009.
Pharmaceutics and Pharmacy Practice, J.B. Lippincott Co., Philadelphia, Pa., Banker and Chalmers, eds., pp. 238-250 (1982).
Riganti et al., "Apocynin: Molecular Aptitudes" 2008.
Riganti et al., "The NADPH oxidase inhibitor apocynin (acetovanillone) induces oxidative stress" 2006.
Seo et al., "NADPH Oxidase Mediates Depressive Behavior Induced by Chronic Stress in Mice" 2012.
Singhal Pravin C et al., "Morphine modulates migration of monocytes", Nephron, vol. 73, No. 4, 1996, pp. 526-531.
Sorg et al., "Inhibition of Astrocyte Glutamate Uptake by Reactive Oxygen Species: Role of Antioxidant Enzymes" 1997.
Tehila Beiser et al., "The role of Oxidative Stress in Cocaine Addiction", Apr. 1, 2019, p. 18, right-hand col. para. 2 p. 20.
Uys et al., "Cocaine-Induced Adaptations in Cellular Redox Balance Contributes to Enduring Behavioral Plasticity", Neuropsychopharmacology, 36, pp. 2551-2560, 2011.
Vejrazka et al., Biochimica et Biophysica Acta "Apocynin inhibits NADPH oxidase in phagocytes but stimulates ROS production in non-phagocytic cells", vol. 1722, Issue 2, Mar. 11, 2005, pp. 143-147.

*Primary Examiner* — Joseph K McKane
*Assistant Examiner* — Quincy McKoy
(74) *Attorney, Agent, or Firm* — NORTON ROSE FULBRIGHT US LLP

(57) ABSTRACT

Certain embodiments are directed to methods of treating or preventing an addictive behavior in a subject, said method comprising administering to said subject an effective amount of a DMTU or a composition comprising same.

22 Claims, 9 Drawing Sheets

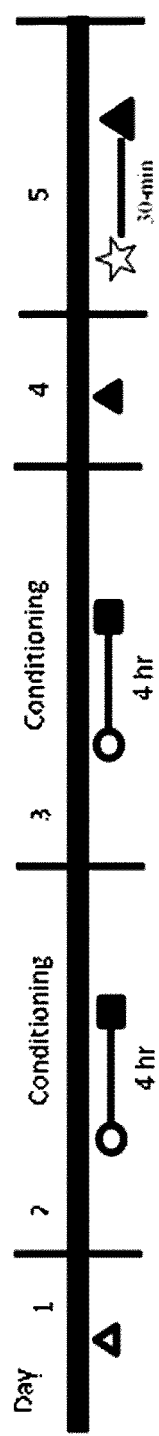
FIG. 3
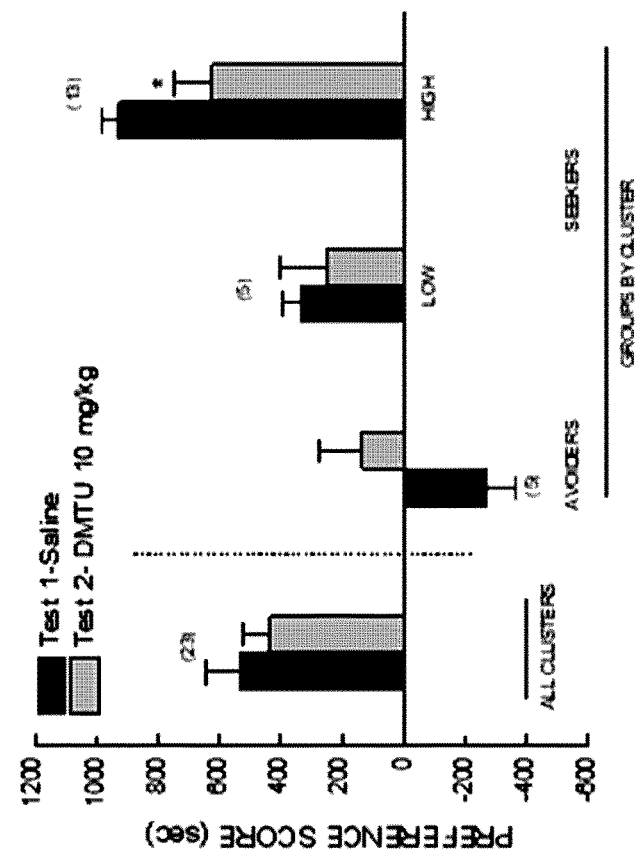
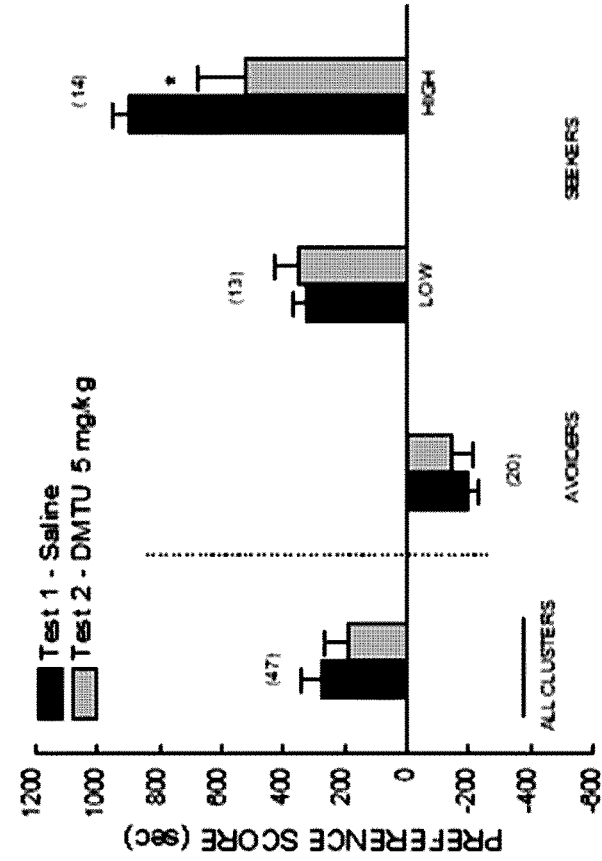
FIG. 4A-B

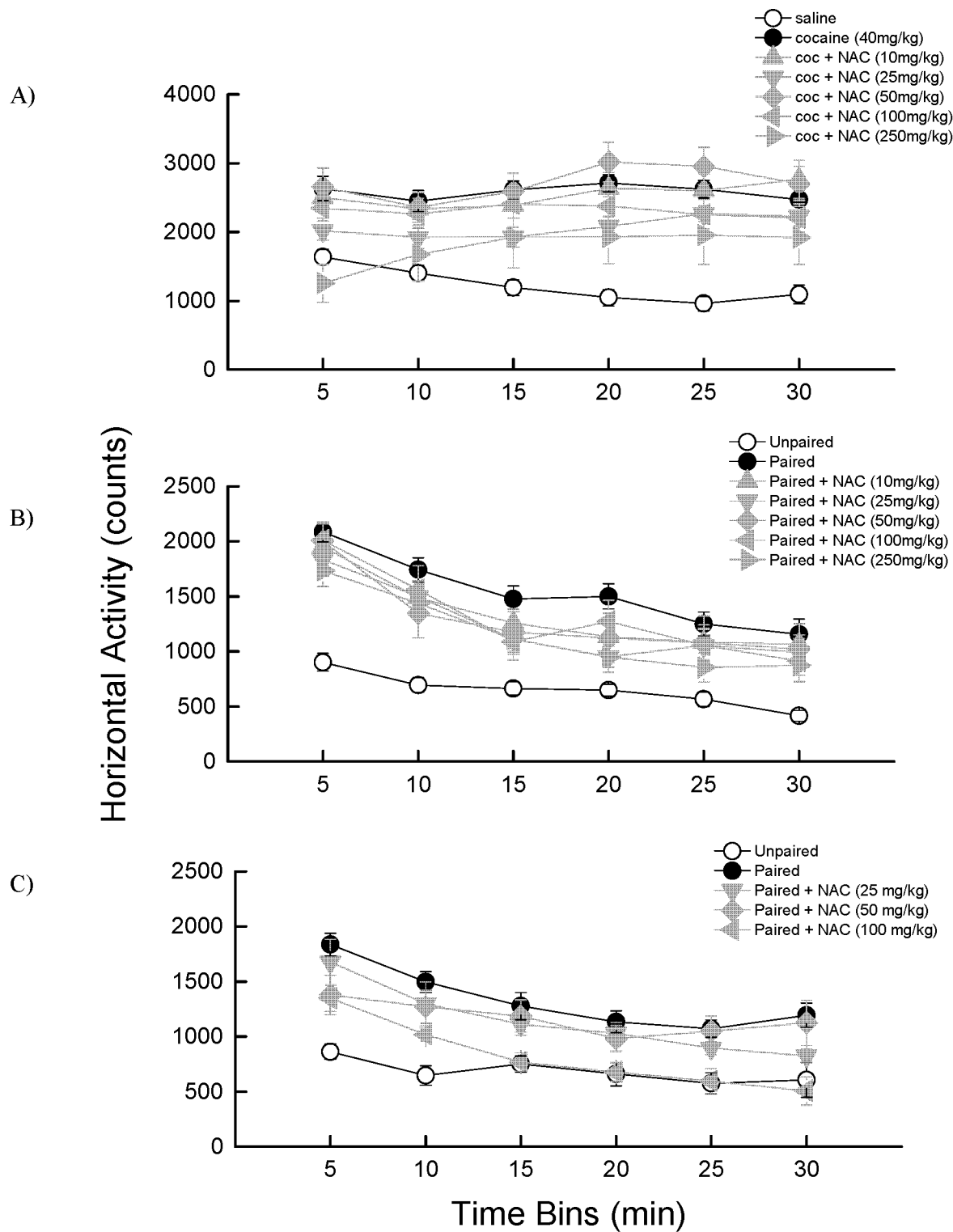
FIG. 5A-C

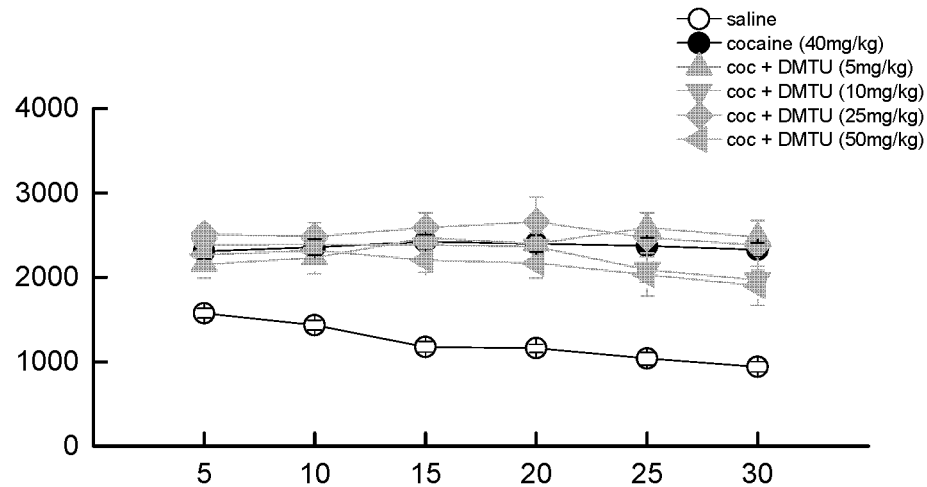
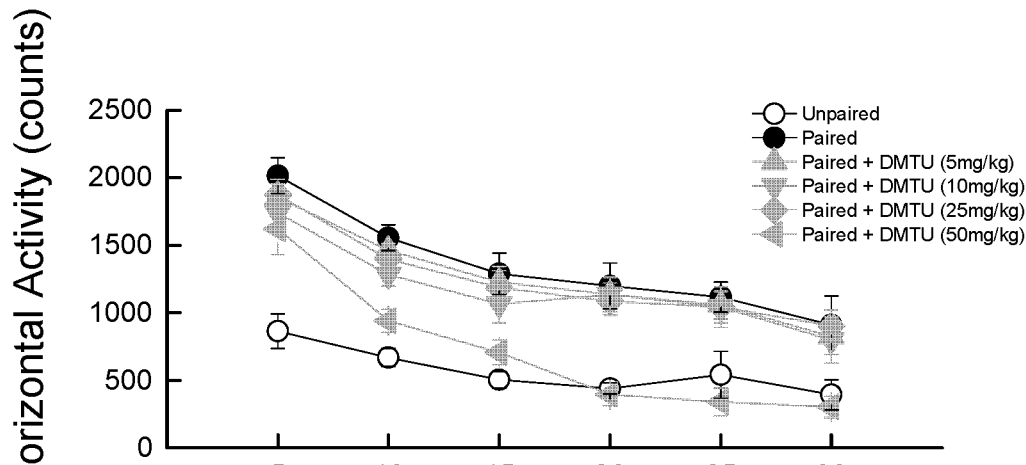
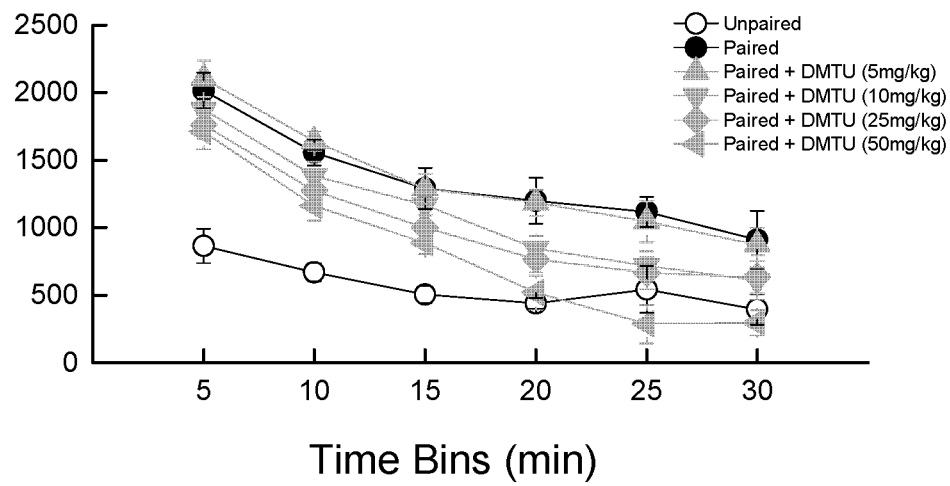
FIG. 6A-C

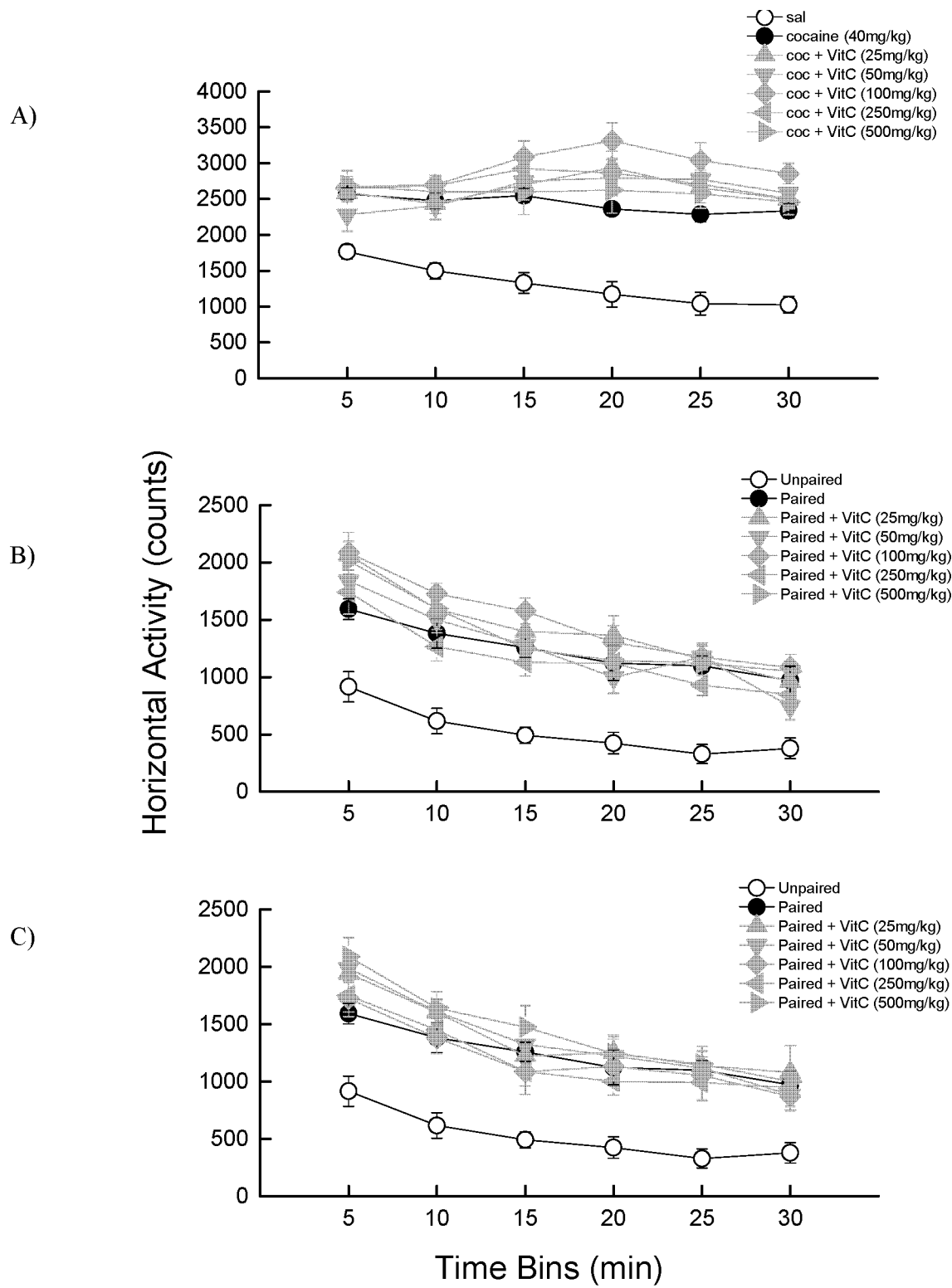
FIG. 7A-C

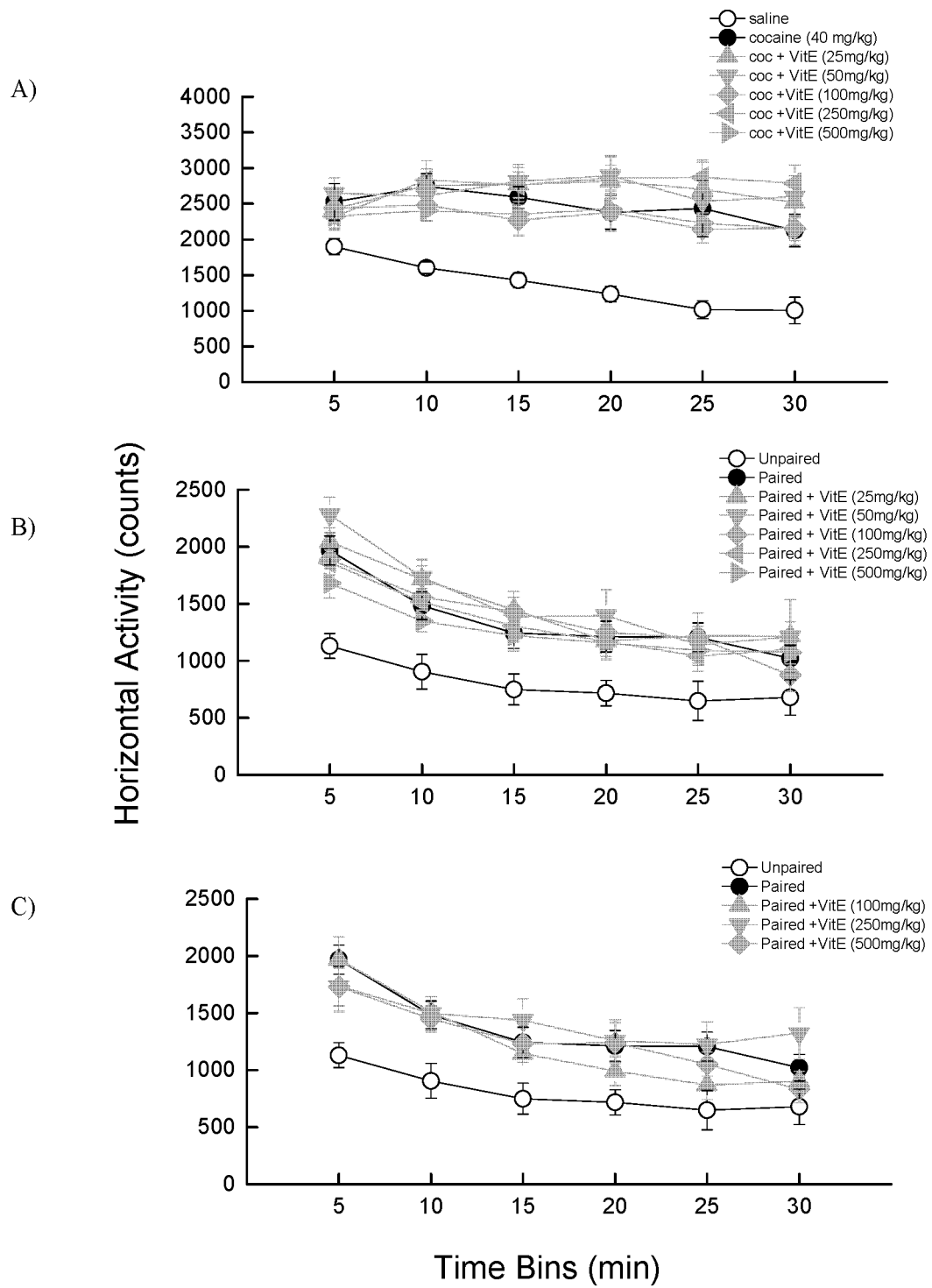
FIG. 8A-C

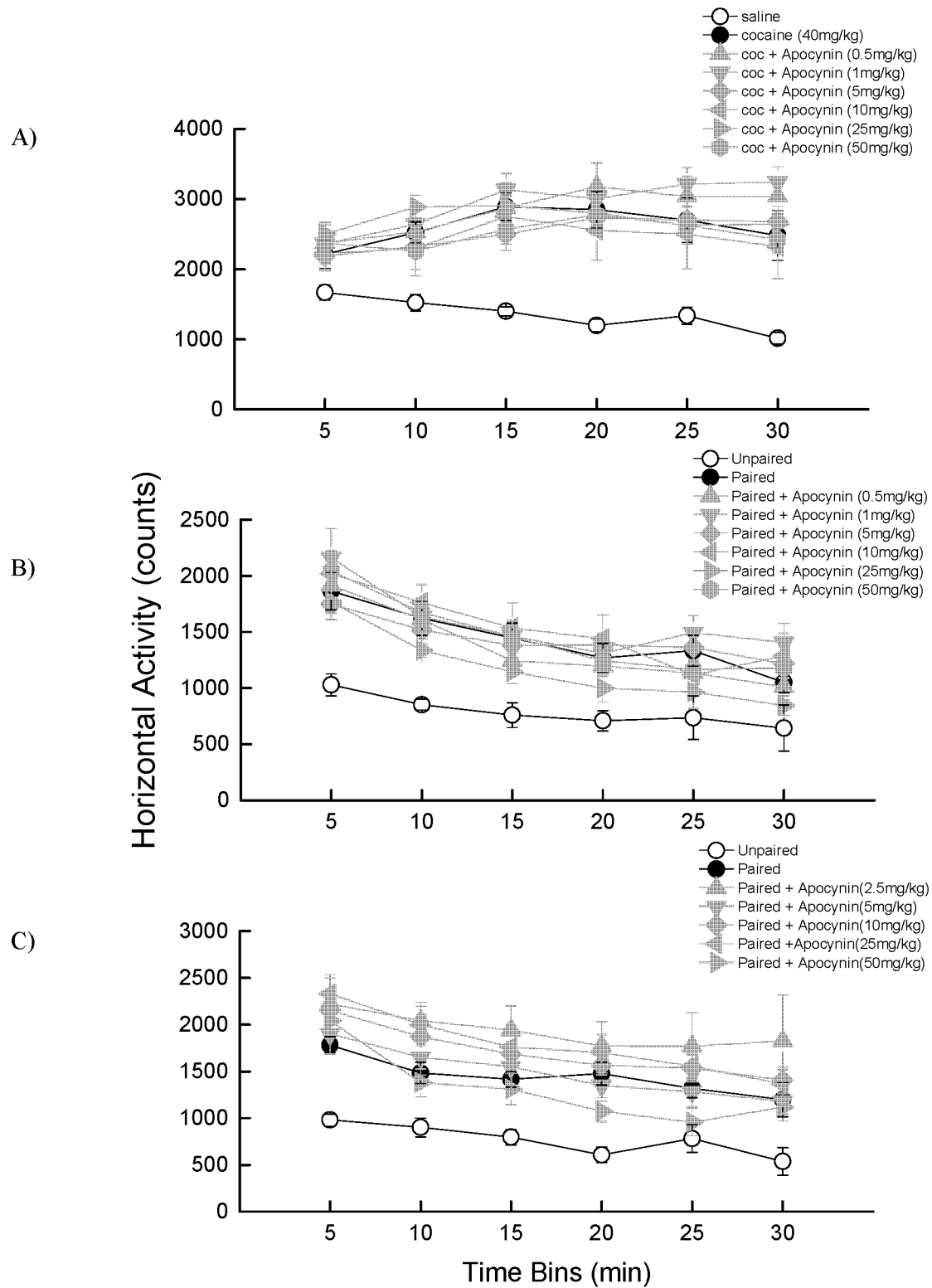
FIG. 9A-C

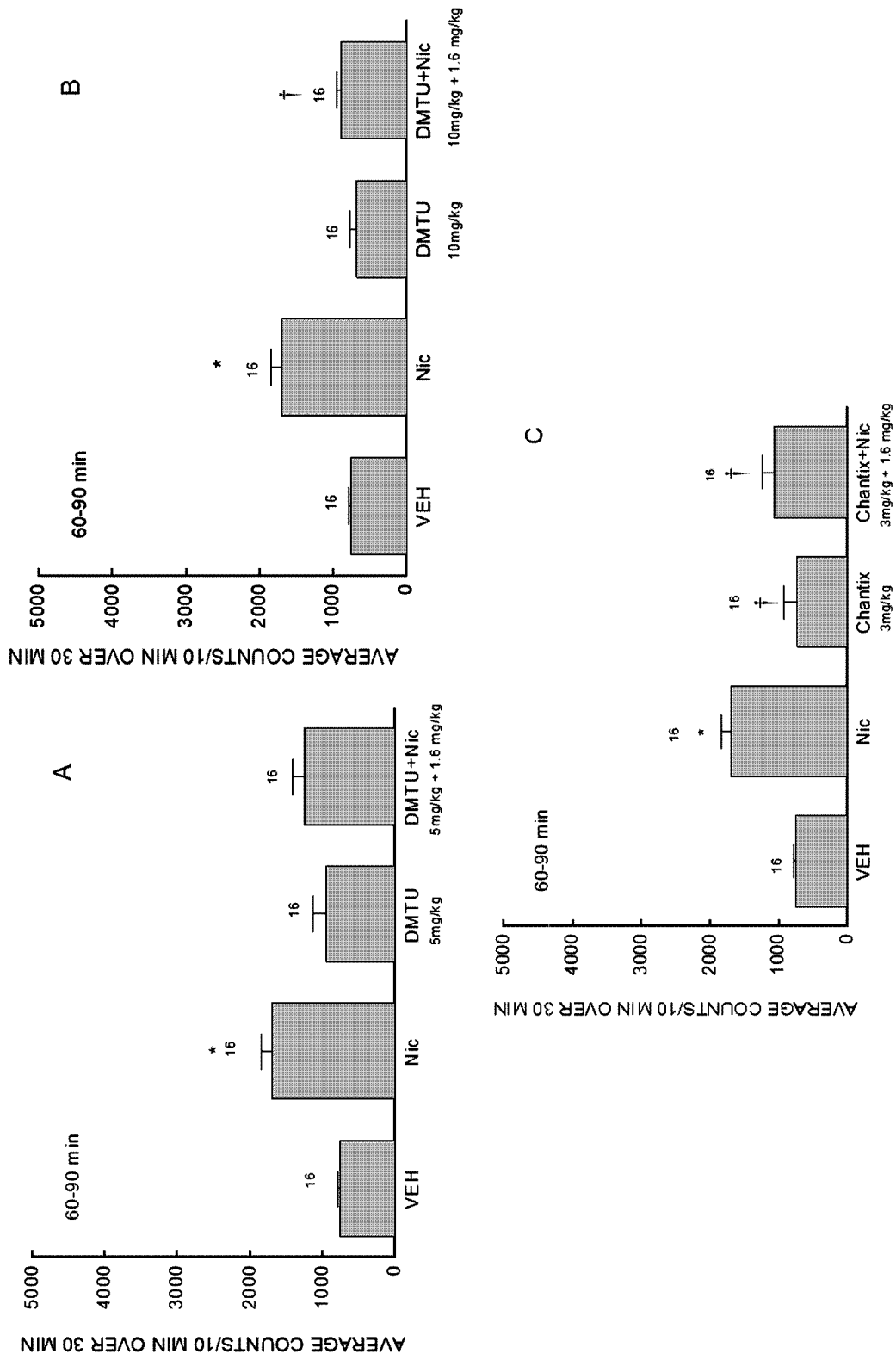
FIG. 11A-C

COMPOSITIONS FOR TREATMENT OF SUBSTANCE USE DISORDER

CROSS-REFERENCE TO RELATED APPLICATIONS

This application is a national phase under 35 U.S.C. § 371 of International Application No. PCT/US2020/070291, filed Jul. 17, 2020, which claims the benefit of priority to U.S. Provisional Patent Application No. 62/876,532, filed Jul. 19, 2019, the entire contents of each of which are hereby incorporated by reference in their entirety.

STATEMENT REGARDING FEDERALLY FUNDED RESEARCH

This invention was made with government support under HHSN271201800031C and HHSN271201300001 awarded by the National Institutes of Health. The government has certain rights in the invention.

BACKGROUND

Certain embodiments of the invention are related to the field of medicine, in particular treatment of substance use.

Addiction is a physical or psychological dependence on a substance or an activity that may be harmful to the addict or can interfere with the addict's normal life.

Many drugs, both illegal and legal, which may include prescription drugs, can cause a physical or psychological dependence. Illicit drug addiction has a negative impact on society as addicts tend to resort to crime to support their addiction. Examples of illegal addictive substances include: cocaine, marijuana, opiates, sedatives and amphetamines. Legal substances that can be addictive include caffeine, alcohol, nicotine, and some prescription medications.

Activities that can become addictive to the point that they interfere with the addict's normal life include: gambling, shopping, exercise, work, computer usage, internet usage, computer games, sex, cleaning and washing.

Cocaine is a commonly used, addictive, illicit drug, obtained from the leaves of the coca plant. Cocaine addiction is characterized by obsessive, compulsive drug consumption that is difficult to stop. Statistically, cocaine addicts that manage to stop their addiction exhibit a high rate of relapse as craving for cocaine remains after stopping use. In addicted users, abrupt stopping of cocaine usage can bring about withdrawal symptoms, such as paranoia, depression, sleep disturbances and anxiety. Cocaine addiction is commonly treated by psychotherapy in rehabilitation centers, but dropout rates in such programs are high. The withdrawal symptoms and the vulnerability to relapse make it difficult to succeed in providing a long-term cure for cocaine addiction.

In many addicts, cue reactivity is exhibited. Cue reactivity is a phenomenon in which an addict physiologically or psychologically responds to a stimulus related to his addiction. In many situations, exposure to a cue associated with an addict's past use of cocaine will elicit and/or increase craving in an addict. For example, for a person addicted to cigarette smoking or a person in a process of breaking an addiction to cigarette smoking, the smell of cigarette smoke or seeing another person light a cigarette may induce craving for a cigarette. For an alcoholic or alcoholic in rehabilitation, the sound of wine glasses clinking may induce a craving for alcohol. For a cocaine addict, seeing drug related paraphernalia may be a cue that induces craving. Cue reactivity may continue for long after the addictive behavior has stopped, increasing a risk that an addict may return to his or her addiction. Many rehabilitation programs encourage addicts to avoid "addiction" cues to facilitate their rehabilitation process.

Previous attempts to develop therapeutics to prevent relapse following psychostimulant abstinence have targeted dopamine (DA) neurotransmission, based on knowledge that DA is the chemical released during natural and drug reward. Review of the literature confirms that antidepressants and other medications targeting DA have failed in trials or produced untoward outcomes (EMCDDA Literature review, 2005). These trials likely failed because interference with DA neurotransmission does not prevent activation of drug-associated memory, per se, it only prevents or diminishes activation of DA. Since this effect is incomplete, it may lead to escalation of drug-seeking behavior, and increase the probability of cardiovascular side-effects upon relapse drug use.

There remains a need for additional method for treating addictions, such as cocaine addiction.

SUMMARY

Recovery from drug addiction is hampered by the formation of abnormally strong drug memories during drug use that persist after abstinence. These persistent memories lead to relapse of the addiction. If the expression of these memories could be prevented or suppressed, relapse would be less likely. In two preclinical mouse models of substance use disorder, the antioxidant N,N'-dimethylthiourea (DMTU), blocked expression of cocaine-stimulated memory formation. This effect was selective for mice exhibiting strong drug-associated memories. Thus, DMTU may prevent relapse following cocaine abstinence. No other medications are available with this potential action. DMTU does not target DA neurotransmission directly, but instead is hypothesized to block consolidation and reactivation of drug-associated memories by virtue of inhibiting redox signals that are not activated during normal memory. Acting via this mechanism, DMTU would stabilize drug seeking in response to drug-associated memories and not increase the probability of untoward effects to a drug used during abstinence.

As demonstrated herein, the inventors of the invention disclosed in the present application have discovered that DMTU is efficient in treating a variety of additive behaviors and are additionally useful in suppressing relapse into addiction in subjects susceptible to regressing back to addictive state.

Thus, in a first aspect of the invention there is provided a method of treating or preventing an addictive behavior in a subject, said method comprising administering to said subject an effective amount of a DMTU or a composition comprising same. The subject may be any animal, including a mammal, and particularly, a human.

In some embodiments, the addictive behavior is exhibited by said subject, following an unintentional or intentional exposure of said subject to at least one stimulus, trigger or cue, which induces in said subject an addictive behavior. In other words, the at least one stimulus may cause the subject to relapse into full or partial addiction to at least one agent or behavior.

In some embodiments, said subject to be treated in accordance with the invention has been previously reduced or eliminated use of the addictive agent or practice of the addictive or compulsive behavior in response to treatment with an effective amount of an anti-addiction treatment, and/or wherein the subject is no longer exposed to an effective amount of the anti-addiction treatment.

Thus, the invention also contemplates a method for preventing relapse into addiction. The method of the invention is also useful in reducing the addictive effect of re-exposure or continuous exposure to at least one agent, behavior or stimulus which induces the addictive behavior in an addicted subject or in a subject having a risk of developing an addiction. In some embodiments, the addiction is not induced by re-exposure or continuous exposure to at least one agent or behavior.

In another aspect, the invention provides a method of treating or preventing or reducing the probability of relapse to addiction, relapse use of an addictive agent or practice of an addictive or compulsive behavior in a subject, the method comprising administering to said subject in need thereof an effective amount of DMTU.

In some embodiments, said subject to be treated has undergone a period of abstinence from, or reduced use of an addictive agent or behavior.

The invention similarly provides a method of preventing an addiction, the method comprising identifying a subject having a predisposition to addiction or who is at risk of developing an addiction; and providing to said subject an effective amount of DMTU. In accordance with this aspect of the invention, in order to determine a subject's state of being at risk of developing an addiction, or predisposition to addiction, the subject is first diagnosed by available diagnostic means, observation or analysis by a medical care provider. Predisposition factors may be genetic, biological/pharmacological and social factors.

As used herein, the term "treatment" or any variation thereof refers to obtaining beneficial or desired results, including and preferably clinical results. The treatment according to the invention involves optionally either the reducing or amelioration of any one symptom or condition which is indicative or characteristic of addiction or relapse, or delaying the progression of such a symptom or condition. In some embodiments, the treatment results in withdrawal from addiction.

The treatment with DMTU may be achieved by systemic administration, DMTU passes the blood-brain barrier. In some embodiments of the invention, DMTU is administered parenterally, for example, via intravenous administration. In other embodiments, DMTU is administered orally or intranasally.

Similarly, the term "prevention" or any variation thereof refers to arresting or delaying the onset or recurrence of a symptom or condition associated with addiction, or preventing the occurrence or recurrence of such symptoms.

DMTU is typically administered in an amount effective to achieve a desired result of changing addiction-related behavior of the subject. The "effective amount" as used herein is determined by such considerations as may be known in the art. The amount must be effective to achieve the desired effect on addiction, depending, inter alia, on the type and severity of the addiction to be treated and the treatment regime. The "effective amount" or "therapeutically effective amount" is the amount effective to achieve the specified result of changing addiction-related behavior by a subject, the sufficient to affect a desired biological or psychological effect. As generally known, an effective amount depends on a variety of factors including DMTU distribution profile within the body, a variety of pharmacological parameters such as half-life in the body, on undesired side effects, if any, on factors such as age and gender, etc. It should be emphasized, however, that the invention is not limited to any particular dose.

In some embodiments, the addiction to be treated or prevented as disclosed herein is a physical dependence to an agent (an addictive agent) or to a particular behavioral pattern. The addiction expressing a physical dependence may be to an agent generally selected from illicit drugs, prescription drugs (and over the counter (OTC) drugs), alcohol or any combination thereof, which agent is referred to herein as the "addictive agent" or "stimulus". An addictive behavior is exhibited by the subject following exposure of the subject to that agent or stimulus, the agent or stimulus inducing the addictive behavior. Generally speaking, the agent causes a recurring compulsion by an individual to engage in use and abuse of the agent, despite harmful consequences to the individual's health, mental state or social life. The term "addictive behavior" similarly refers to a behavioral compulsion, such as gambling, and compulsive overeating, as further detailed herein below.

In some embodiments, the addiction is caused by an addictive agent, being optionally selected amongst addictive recreational drugs and addictive medications.

In additional embodiments, the addictive agent or stimulus is selected from alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine.

In some embodiments, the addiction is to cocaine.

The invention also provides a method for affecting memory retrieval in a subject prone to relapse into addiction or for diminishing, suppressing or minimizing addictive behavior, the method comprising administering to the subject DMTU prior, during or after intentional or unintentional exposure to a stimulus.

As used herein, the "stimulus" refers to a trigger or a cue which may be any material or any event captured by any one of a subject's senses (smells, visions, touch, etc.), or any other factor (such as thoughts) which is capable of triggering, inciting, exerting or forcing a subject to express an addictive behavior. The stimulus, for example, may be re-exposure to an element of the addiction which is familiar to the subject and which exerts in said subject a feeling or a thought which may eventually lead to relapse or repeated behavior. For example, where addiction to alcohol is concerned, the stimulus may be the sight of another person consuming alcohol, or the mere odor of an alcoholic beverage. In another example, where the addiction is a compulsive behavior, such as gambling, the stimulus may be the subject's belief that he/she has the best chance of winning.

The invention further contemplates uses and compositions comprising DMTU for treating or prevention an addictive behavior in a subject.

The invention also provides kits and commercial packages comprising DMTU and instructions for use.

The various embodiments can use DMTU in the manufacture of a medicament for use for treating or prevention an addictive behavior in a subject; for mitigating relapse into addiction of a subject; for reducing the addictive effect of re-exposure or continuous exposure to at least one agent, behavior, or stimulus; treating or preventing or suppressing relapse to addiction, relapse use of an addictive agent or practice of an addictive or compulsive behavior in a subject; or preventing an addiction in a subject, the method comprising identifying a subject having a predisposition to addiction or who is at risk of developing an addiction.

Certain embodiments are directed to methods or the use of DMTU in treating or preventing an addictive behavior in a subject, the method or use comprising administering to said subject a composition comprising an effective amount of N,N' dimethylthiourea (DMTU). The addictive behavior is or can be exhibited by the subject following exposure of the subject to at least one stimulus, the stimulus inducing the addictive behavior. The stimulus can be selected from, but not limited to alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine. DMTU can be administered at 1 to 100 mg/kg. DMTU is or can be administered orally, intratracheally, intravenously, intramuscularly, intraperitoneally, percutaneously, topically, or subcutaneously. In certain aspects, the subject is administered DMTU on a regular schedule. In a further aspect, the subject is administered DMTU daily, at least once, twice, three times a day, or weekly.

Embodiments are directed to methods or the use of DMTU for mitigating relapse into addiction of a subject, the method comprising administering to said subject a composition comprising an effective amount of N,N'dimethylthiourea (DMTU). In certain aspects, DMTU is administered at 1 to 100 mg/kg. DMTU is or can be administered orally, intratracheally, intravenously, intramuscularly, intraperitoneally, percutaneously, topically, or subcutaneously. In certain aspects, the subject is administered DMTU on a regular schedule. In a further aspect, the subject is administered DMTU daily, at least once, twice, three times a day, or weekly.

Embodiments are directed to methods or use of DMTU for reducing the addictive effect of re-exposure or continuous exposure to at least one agent, behavior, or stimulus which induces addictive behavior in a subject, wherein the subject is an addict or having a risk of developing addiction, the method comprising administering to said subject a composition comprising an effective amount of N,N'dimethylthiourea (DMTU). DMTU is administered at 1 to 100 mg/kg. DMTU can be administered orally, intratracheally, intravenously, intramuscularly, intraperitoneally, percutaneously, topically, or subcutaneously. In certain aspects, the subject is administered DMTU on a regular schedule. In a further aspect, the subject is administered DMTU daily, at least once, twice, three times a day, or weekly.

Embodiments are directed to methods or use of DMTU for treating or preventing or suppressing relapse to addiction, relapse use of an addictive agent or practice of an addictive or compulsive behavior in a subject, the method comprising administering to said subject a composition comprising an effective amount of N,N'dimethylthiourea (DMTU). DMTU is or can be administered at 1 to 100 mg/kg. DMTU is or can be administered orally, intratracheally, intravenously, intramuscularly, intraperitoneally, percutaneously, topically, or subcutaneously. In certain aspects, the subject is administered DMTU on a regular schedule. In a further aspect, the subject is administered DMTU daily, at least once, twice, three times a day, or weekly.

Embodiments are directed to methods or use of DMTU for preventing an addiction in a subject, the method comprising identifying a subject having a predisposition to addiction or who is at risk of developing an addiction and administering to the subject an effective amount of N,N'dimethylthiourea (DMTU). In certain aspects, the addiction is a physical dependence to an addictive agent or to an addictive behavior. The addictive agent is or can be selected from the group consisting of addictive recreational drugs and addictive medications. An addictive agent can be selected from the group consisting of alcohol, caffeine, nicotine, cannabis and cannabis derivatives, opiates and morphine-like compounds, phencyclidine and phencyclidine-like compounds, sedative hypnotics, psychostimulants, amphetamines and amphetamine-related drugs. In a further aspects, the addictive agent can be selected from the group consisting of alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine. In a particular aspect, the addictive agent is cocaine. The addictive agent can be a pain-killer or a combination of pain-killers. The pain-killer can be selected from the group consisting of alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol and tilidine. In certain aspects, the addictive agent is selected from the group consisting of alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tilidine and tramadol. The addictive behavior is or can be selected from the group consisting of obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking. In certain aspects, the addiction is to more than one of an addictive agent and/or addictive behavior. DMTU is or can be administered at 1 to 100 mg/kg. DMTU is or can be administered orally, intratracheally, intravenously, intramuscularly, intraperitoneally, percutaneously, topically, or subcutaneously. In certain aspects, the subject is administered DMTU on a regular schedule. In a further aspect, the subject is administered DMTU daily, at least once, twice, three times a day, or weekly.

Embodiments are directed to methods or the use of DMTU for affecting memory retrieval in a subject prone to relapse into addiction or for diminishing, suppressing or minimizing addictive behavior, the method comprising administering to said subject an effective amount of N,N' dimethylthiourea (DMTU). prior, during or after intentional or unintentional exposure to a stimulus. DMTU is or can be administered at 1 to 100 mg/kg. DMTU is or can be administered orally, intratracheally, intravenously, intramuscularly, intraperitoneally, percutaneously, topically, or subcutaneously. In certain aspects, the subject is administered DMTU on a regular schedule. In a further aspect, the subject is administered DMTU daily, at least once, twice, three times a day, or weekly.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 3. Conditioned place preference timeline.

FIGS. 4A-B. Effect of DMTU on cocaine-conditioned place preference by administration of either 5 mg/kg DMTU (panel A) or 10 mg/kg DMTU (panel B). Black bars represent mean preference score on Test 1 when no DMTU had been administered, and grey bars represent mean preference scores on Test 2 after treatment with either 5 mg/kg DMTU (panel A) or 10 mg/kg DMTU (panel B). Mean preference scores (±SE) of combined clusters are represented left of the dotted line in A and in B, whereas mean preference scores (±SE) of each of the clusters separately (Avoider, Low Seeker, High Seeker) are depicted to the right of the dotted line in A and B.

FIGS. 5A-C. N-acetylcysteine modulates the cocaine-conditioned locomotor response. (A) N-acetylcysteine had no effect on the acute hyperlocomotor effect of cocaine, though (B) 250 mg/kg NAC attenuated acquisition and (C) 100 mg/kg NAC attenuated expression of the cocaine-conditioned locomotor response. Each point depicts the horizontal activity (counts) using 5 min time bins across 30 min±S.E. 7-24 mice.

FIGS. 6A-C. Dimethylthiourea modulates the cocaine-conditioned locomotor response. (A) Dimethylthiourea had no effect on the acute hyperlocomotor effect of cocaine, though 50 mg/kg dimethylthiourea attenuated (B) acquisition and (C) expression of the cocaine-conditioned locomotor response. Each point depicts the horizontal activity (counts) using 5 min time bins across 30 min±S.E. 8 mice.

FIGS. 7A-C. Vitamin C modulates cocaine-induced locomotion. (A) 100 mg/kg vitamin C facilitated the acute hyperkinetic effect of cocaine, (B) 100 mg/kg vitamin C acquisition facilitated acquisition of the conditioned response, and (C) vitamin C had no effect on expression of the cocaine-conditioned locomotor response. Each point depicts the horizontal activity (counts) using 5 min time bins across 30 min±S.E. 8 mice.

FIGS. 8A-C. Vitamin E does not modulate cocaine-induced hyperlocomotion or the conditioned response. (A) Vitamin E had no effect on the acute cocaine-induced hyperlocomotor effect. In tests for conditioning, (B) vitamin E had no effect on the acquisition of the conditioned response and (C) no effect on expression of the conditioned response. Each point depicts the horizontal activity (counts) using 5 min time bins across 30 min±S.E. 7-8 mice.

FIGS. 9A-C. Apocynin does not attenuate the cocaine-conditioned response. (A) Apocynin had no effect on the acute cocaine-induced hyperlocomotor response. In tests for conditioning, (B) apocynin had no effect on the acquisition of the conditioned response, whereas (C) 25 mg/kg apocynin facilitated expression of the conditioned response, during the first 15 min. Each point depicts the horizontal activity (counts) using 5 min time bins across 30 min±S.E. 7-8 mice.

FIG. 11. Locomotor activity test results when mice were administered either vehicle or DMTU (5 mg/kg, A or 10 mg/kg, B) or Chantix (3 mg/kg, C). Nicotine induced stimulant activity was observed in mice in the last 60 min of a 2-h test. DMTU in a dose of 10 mg/kg significantly reduced nicotine-induced stimulant locomotor response (B). A 3 mg/kg dose of Chantix either alone or with nicotine significantly attenuated locomotor activity non-selectively (C). Each bar represents average horizontal activity (counts)+S.E. for a period 60-90 min of the locomotor activity test for the different experimental groups: vehicle, nicotine (1.6 mg/kg), 5 mg/kg DMTU (A), 5 mg/kg DMTU+ Nicotine (1.6 mg/kg), 10 mg/kg DMTU, 10 mg/kg DMTU (B)+Nicotine (1.6 mg/kg), 3 mg/kg Chantix (C), 3 mg/kg Chantix+Nicotine (1.6 mg/kg) (n=16/experimental group). * represents significant difference from the vehicle group, and † represents significant difference from the nicotine group, p<0.05.

DESCRIPTION

Figure 1:
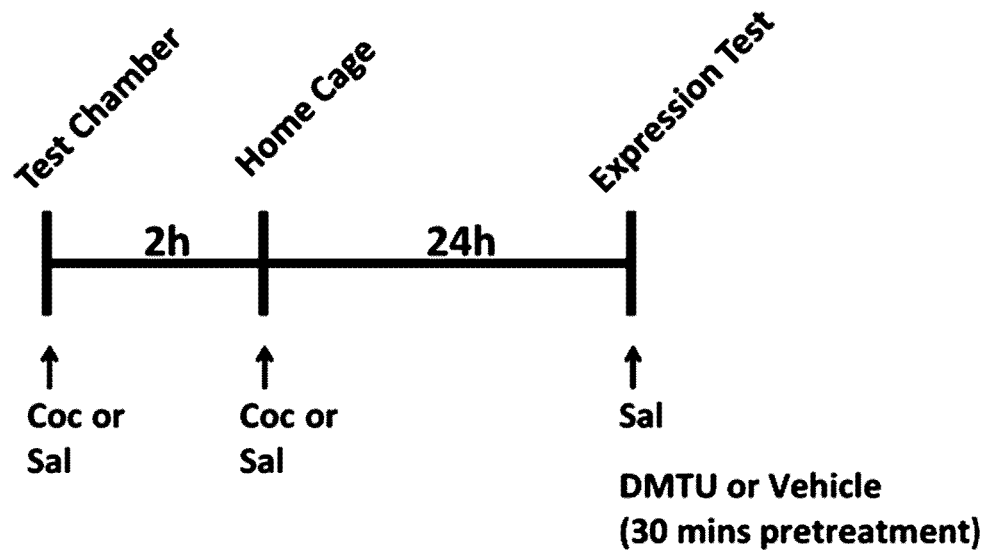
FIG. 1. Cocaine-conditioned locomotor activity timeline.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Acute and chronic cocaine exposure induces changes in oxidative stress levels in the brain (Dietrich et al., 2005; Uys et al., 2011). Preliminary results suggested that neuroplasticity induced by acute cocaine exposure in a novel environmental context facilitated a conditioned behavioral effect response, which is believed could be modulated by altering the redox state potential. The antioxidant treatments were chosen for their ability to provide a pro-reducing redox state and to attenuate the generation of oxidative stress at different intracellular and extracellular locations. However, of all the antioxidant treatments that were administered, only NAC and DMTU significantly attenuated the acquisition and/or expression of the cocaine-conditioned locomotor response, as shown in FIG. 5. NAC and DMTU selectively attenuated expression independently from their acute hypokinetic effects, represented by an ED50:AD50 ratio of 1.2731 and 4.676, respectively. Overall this would suggest that although antioxidant treatments may modulate the conditioned response, redox state potential does not fully predict changes in the cocaine-conditioned behavior.

It has previously been reported that NAC could impact cocaine-induced behavioral responses through its effect on the cysteine-glutamate transporter and its modulation of metaplasticity (Moussawi et al., 2009). Unlike NAC, DMTU acts as a non-thiolic free radical scavenger, independently of the cysteine-glutamate transporter system. Previous studies have acknowledged DMTU's ability to decrease cocaine-mediated increase in reactive oxygen species and damage (Labib et al., 2003); however, this compound has not yet been utilized prevent cocaine-induced learned behavior. DMTU effectively eliminates free radicals, though it has also previously been shown to prevent the inhibition of astroglial glutamate uptake caused by reactive oxygen species (Sorg et al., 1997). This could suggest a common mechanism by which NAC and DMTU both facilitate a pro-reducing redox state but possibly more importantly assist in the regulation of glutamatergic signaling associated with conditioned behavior. It is also important to note that unlike NAC, DMTU failed to affect the acute hyperlocomotor response induced by cocaine yet significantly attenuated both the acquisition and expression of the conditioned behavior. This would suggest that neither the acquisition nor expression of the cocaine-conditioned locomotor response is contingent upon cocaine's ability to elicit a hyperlocomotor response acutely.

As shown in FIG. 6, vitamin C, vitamin E, and apocynin failed to attenuate the conditioned locomotor effect. Aside from their select differences in mechanism and sites of action from NAC and DMTU, one possible explanation is that these compounds failed to produce a sufficiently pro-reducing redox environment. Shown in FIG. 6, ascorbic acid exacerbated the hyperkinetic response induced by cocaine acutely. Interestingly, 100 mg/kg vitamin C facilitated acquisition and 25 mg/kg apocynin facilitated expression of the cocaine-conditioned locomotor response, though only during the first 15 min of the expression test. It has been shown that ascorbic acid may produce pro-oxidizing redox state (Ivanova et al., 2013), which would prevent any neuroprotective properties and possibly facilitate the acute cocaine response and conditioned response. Apocynin, likewise, has been shown to have cytotoxic effects through possible increases in oxidative stress (Riganti et al., 2006; Riganti et al., 2008; Vejrazka et al., 2005). Furthermore, ascorbic acid and apocynin share a common effect in their ability to inhibit NADPH oxidase (Moritz et al., 2003). NADPH oxidase has been shown to mediate depressive behavior induced by stress (Seo et al., 2012), which could explain the varied effects. Apocynin was tested to confirm the importance of this possible mechanism, and the behavioral results suggest that inhibition of NADPH oxidase may contribute to the inability to attenuate the conditioned response by these compounds. Vitamin C, vitamin E, and apocynin failed to attenuate the acquisition or expression of the cocaine-conditioned response, further suggesting that modulation of redox state does not fully predict changes in the cocaine-conditioned behavior.

Biochemical results confirm that cocaine induced changes in redox stress and that administration of the test compounds altered the redox state in neuronal tissue. ROS signals may mediate context associations during the development of addiction in a very complex manner; however, it is possible that redox state may not fully predict the conditioned locomotor effects induced by cocaine. Using this paradigm, other drugs of abuse may be tested for conditioned effects in order to determine if the locomotor effect is substance-specific (Badiani, 2013) and if increased redox stress and drug-induced glutamatergic signaling is also correlated. In conclusion, the effect of the antioxidant treatment further supports the potential value of redox modulating compounds as targets for addiction treatment. The results suggest that alteration of redox state may influence neural plasticity dependent alterations in brain mediating addiction and relapse, though only certain antioxidant compounds may be viable targets for addiction treatment medications.

The invention relates to a known compound, N, N'-Dimethylthiourea (DMTU), the inventors have discovered the use of DMTU for the treatment of cocaine addiction and relapse, by virtue of the compound's ability to block expression of the abnormally strong memories associated with cocaine/drug use. The compound essentially blocks expression of the conditioned stimulant effect of cocaine that can lead a previous drug user to relapse.

I. N,N'-DIMETHYLTHIOUREA (DMTU)

N, N'-Dimethylthiourea is known to be an antioxidant and has been studied preclinically for antioxidant effects (not in the context of substance use disorders). Other antioxidants (primarily N-Acetylcysteine) have been studied in the context of substance abuse, with mixed results. The inventors theorized that altering the cellular redox state by antioxidant therapy may have an impact on mediating addiction and relapse. Consequently, several known antioxidants where studied in mouse models. DMTU was the only compound that blocked expression of cocaine-stimulated memory formation, thus having the potential to prevent relapse following cocaine abstinence. They also found that the effect was selective for mice exhibiting strong drug-associated memories (most likely to relapse). Since other known antioxidants were not effective in these studies, the activity of DMTU was unexpected.

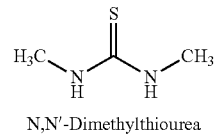

N,N'-Dimethylthiourea

II. METHOD OF TREATING SUBSTANCE USE

As demonstrated herein, the inventors have discovered that DMTU is efficient in treating a variety of additive behaviors and are additionally useful in suppressing relapse into addiction in subjects susceptible to regressing back to addictive state. Thus, in a first aspect of the invention there is provided a method of treating or preventing an addictive behavior in a subject, said method comprising administering to said subject an effective amount of a DMTU or a composition comprising same. The subject may be any animal, including a mammal, and particularly, a human.

In some embodiments, the addictive behavior is exhibited by said subject, following an unintentional or intentional exposure of said subject to at least one stimulus, trigger or cue, which induces in said subject an addictive behavior. In other words, the at least one stimulus may cause the subject to relapse into full or partial addiction to at least one agent or behavior.

In some embodiments, said subject to be treated in accordance with the invention has been previously reduced or eliminated use of the addictive agent or practice of the addictive or compulsive behavior in response to treatment with an effective amount of an anti-addiction treatment, and/or wherein the subject is no longer exposed to an effective amount of the anti-addiction treatment.

Thus, the invention also contemplates a method for preventing relapse into addiction. The method of the invention is also useful in reducing the addictive effect of re-exposure or continuous exposure to at least one agent, behavior or stimulus which induces the addictive behavior in an addicted subject or in a subject having a risk of developing an addiction. In some embodiments, the addiction is not induced by re-exposure or continuous exposure to at least one agent or behavior.

In another aspect, the invention provides a method of treating or preventing or reducing the probability of relapse to addiction, relapse use of an addictive agent or practice of an addictive or compulsive behavior in a subject, the method comprising administering to said subject in need thereof an effective amount of DMTU.

In some embodiments, said subject to be treated has undergone a period of abstinence from, or reduced use of an addictive agent or behavior.

The invention similarly provides a method of preventing an addiction, the method comprising identifying a subject having a predisposition to addiction or who is at risk of developing an addiction; and providing to said subject an effective amount of DMTU. In accordance with this aspect of the invention, in order to determine a subject's state of being at risk of developing an addiction, or predisposition to addiction, the subject is first diagnosed by available diagnostic means, observation or analysis by a medical care provider. Predisposition factors may be genetic, biological/pharmacological and social factors.

The treatment with DMTU may be achieved by systemic administration, DMTU passes the blood-brain barrier. In some embodiments of the invention, DMTU is administered parenterally, for example, via intravenous administration. In other embodiments, DMTU is administered orally or intranasally.

Generally speaking, addiction is defined as an uncontrolled and compulsive use (or abuse) of an agent or a behavioral pattern which is considered as an addictive behavior, even where the addictive behavior presents no harm to the subject practicing the behavior or to any other person associated with the subject. Within the scope of the present invention, the addictive behavior to be controlled, suppressed, minimized or diminished (by way of treatment or prevention) may be of two types: physiological and psychological. Addictions in general often express both physical and psychological features.

In some embodiments, the addiction to be treated or prevented as disclosed herein is a physical dependence to an agent (an addictive agent) or to a particular behavioral pattern. The addiction expressing a physical dependence may be to an agent generally selected from illicit drugs, prescription drugs (and over the counter (OTC) drugs), alcohol or any combination thereof, which agent is referred to herein as the "addictive agent". Generally speaking, the agent causes a recurring compulsion by an individual to engage in use and abuse of the agent, despite harmful consequences to the individual's health, mental state or social life. The term "addictive behavior" similarly refers to a behavioral compulsion, such as gambling, and compulsive overeating, as further detailed herein below.

In some embodiments, the addiction is caused by an addictive agent, being optionally selected amongst addictive recreational drugs and addictive medications.

In some embodiments, the addictive agent is selected from alcohol, caffeine, nicotine, cannabis and cannabis derivatives, opiates and morphine-like compounds, phencyclidine and phencyclidine-like compounds, sedative hypnotics, psycho-stimulants, amphetamines and amphetamine-related drugs.

In additional embodiments, the addictive agent is selected from alcohol, caffeine, nicotine, cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine.

In other embodiments, the addictive agent is selected amongst pain-killer such as alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol, tilidine and any combination of any of the aforementioned agents.

In yet additional embodiments, the addictive agent is selected from alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diampromide, dihydrocodeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tilidine and tramadol.

In some embodiments, the addiction is to cocaine.

In some embodiments, the addiction is in the form of a compulsive behavior (addictive behavior) and may be selected from obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking.

In some embodiments, the addiction is to two or more addictive agents and/or addictive behavior. In some embodiments, one or both of the addictions are to an addictive agent.

As known in the art, memory is the process by which information is encoded, stored, and retrieved and may be generally classified as long term memory (LTM) and short term memory (STM). Short-term memory allows recall of an event or information for a period of several seconds to a minute without rehearsal. The short-term memory generally has a strictly limited capacity and duration, which means that information, is not retained indefinitely. By contrast, long-term memory can store much larger quantities of information for potentially unlimited duration.

Memory consolidation is a category of processes that stabilize a memory trace after the initial acquisition. Reconsolidation is a category of processes in which previously consolidated memories can be made labile again through reactivation of the memory trace.

As such, the methods of the invention present the ability to use DMTU as means to impair the subject's ability to retrieve a memory (or reconsolidation of a memory) of an addictive behavior even after or during unintentional or intentional exposure to a stimulus which otherwise would have caused reactivation of the memory and induce or strengthen the addictive behavior. Memories elicited by a variety of stimuli are reconsolidate after each episode of retrieval or reactivation, thereby allowing these memories to be updated, and disruption of this reconsolidation process by administering DMTU results in a reduction in the motivational properties of stimuli associated previously with pleasure or aversive outcomes.

Thus, the invention also provides a method for affecting memory retrieval in a subject prone to relapse into addiction or for diminishing, suppressing or minimizing addictive behavior, the method comprising administering to the subject DMTU prior, during or after intentional or unintentional exposure to a stimulus.

As used herein, the "stimulus" refers to a trigger or a cue which may be any material or any event captured by any one of a subject's senses (smells, visions, touch, etc), or any other factor (such as thoughts) which is capable of triggering, inciting, exerting or forcing a subject to express an addictive behavior. The stimulus, for example, may be re-exposure to an element of the addiction which is familiar to the subject and which exerts in said subject a feeling or a thought which may eventually lead to relapse or repeated behavior. For example, where addiction to alcohol is concerned, the stimulus may be the sight of another person consuming alcohol, or the mere odor of an alcoholic beverage. In another example, where the addiction is a compulsive behavior, such as gambling, the stimulus may be the subject's belief that he/she has the best chance of winning.

In addiction to drugs of abuse, the stimulus may be the subject's need to achieve a "high" or the subject's belief that by so doing survival of a stressful event may be the only way to overcome.

In some embodiments, the stimulus causing reinstatement of drug abuse or of a compulsive behavior is one or more of stress, re-exposure to a drug or drug-priming, and environmental triggers or cues.

The invention further contemplates uses and compositions comprising DMTU for treating or prevention an addictive behavior in a subject.

III. PHARMACEUTICAL FORMULATIONS AND ADMINISTRATION

In certain embodiments, the invention provides compositions comprising DMTU with one or more of the following: a pharmaceutically acceptable diluent; a carrier; a solubilizer; an emulsifier; a preservative; and/or an adjuvant. Such compositions may contain an effective amount of DMTU. Thus, the use of DMTU that are provided herein in the preparation of a pharmaceutical composition of a medicament is also included.

The compositions employed by the methods of the invention may include pharmaceutically acceptable carriers as described herein, for example, vehicles, excipients, or diluents, which are well-known to those who are skilled in the art and which are readily available to the public. It is preferred that the pharmaceutically acceptable carrier be one which is chemically inert to DMTU and one which has no detrimental side effects or toxicity under the conditions of use.

The choice of carrier will be determined in part by DMTU, as well as by the particular method used to administer the composition. Accordingly, there is a wide variety of suitable formulations of the pharmaceutical composition employed in accordance with the invention. The following formulations for oral, aerosol, parenteral, subcutaneous, intravenous, intramuscular and intraperitoneal administration.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of DMTU, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise DMTU in a flavor, usually sucrose and acacia or tragacanth, as well as pastilles comprising DMTU in an inert base, such as gelatin and glycerin, or sucrose and acacia, emulsions, gels, and the like containing, in addition to DMTU, such carriers as are known in the art.

DMTU employed in accordance with the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. DMTU can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations typically contain from about 0.5 to about 25% by weight of DMTU in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use.

DMTU may be made into injectable formulations. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986).

DMTU may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, or carriers well known in the art.

Acceptable formulation components for pharmaceutical preparations are nontoxic to recipients at the dosages and concentrations employed. In addition to DMTU, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion. When administering the compositions by injection, the administration may be by continuous infusion or by single or multiple boluses. For parenteral administration, DMTU may be administered in a pyrogen-free, parenterally acceptable aqueous solution comprising DMTU in a pharmaceutically acceptable vehicle. A particularly suitable vehicle for parenteral injection is sterile distilled water in which DMTU is formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental administration are also sterile, substantially isotonic and made under GMP conditions.

Doses of DMTU can be between about 0.001 mg/kg and 100 mg/kg body weight, preferably between about 1, 5, 10, 20, 30, 40, 50 and 60, 70, 80, 90, 100, 200, 500 mg/kg body weight (including all values and ranges there between), most preferably between 1 and 10, 1 and 100, or 5 to 50 mg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In additional embodiments, patients may also be administered directly, orally, endoscopically, intratracheally, intravenously, intramuscularly, intraperitoneally, regionally, percutaneously, topically, intrarterially, intravesically, or subcutaneously. Therapeutic compositions or compounds (e.g., DMTU) may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months. The therapeutic compositions or compounds (e.g., DMTU) can be administered 1, 2, 3, 4, 5, 6, or 7 times a day, week, month, or year. The therapeutic compositions or compounds (e.g., DMTU) can be administered daily, weekly, or monthly (i.e., on a regular schedule).

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Application of DMTU in the Treatment of Psychostimulant Addiction and Relapse A. Materials and methods Animals. Male Swiss-Webster mice (Hsd:ND4) were obtained from Envigo Laboratories. Mice were group-housed on a 12-h/12-h light/dark cycle, with access to food and water ad libitum. Mice were tested at approximately 8 weeks of age during the light portion of the cycle. All housing and procedures were in accordance with the guidelines of the Guide for Care and Use of Laboratory Animals (Institute of Laboratory Animal Resources, 1996) and were approved by the University of North Texas Health Science Center Animal Care and Use Committee.

Test Compounds. (−)-Cocaine HCl (40 mg/kg) was obtained from the National Institute on Drug Abuse. N, N'-dimethylthiourea (DMTU) (5 and 10 mg/kg) was obtained from Sigma-Aldrich (St. Louis, Mo.). Cocaine and dimethylthiourea were dissolved in 0.9% saline and administered intraperitoneally (i.p.).

Conditioning and Testing Procedures. Prior to all testing sessions, mice were weighed and labeled according to their treatment. The locomotor activity of mice was measured using the Digiscan apparatus (Omnitech Electronics, Columbus, Ohio) and digital tracking software. Individual mice were placed into a clear acrylic chamber (40.5×40.5× 30.5 cm) that was contained inside a metal frame (49×53×9 cm) lined with photobeam cells. The acrylic chamber and metal frame were enclosed within a sound-suppressing wood cabinet (99.0×49.5×51.0 cm) lined with sheets of insulation and a fan for ambient noise. The photobeams were interrupted by the mouse's activity within the chamber, which was then recorded by the computer. Activity was categorized into basic components which included horizontal activity (counts).

Different groups of Swiss-Webster mice were injected with either 40 mg/kg cocaine (designated Paired) or saline (designated Unpaired) prior to being placed in the locomotor activity testing apparatus for 30 minutes (FIG. 1). Two hours later, Paired mice received saline and Unpaired mice received 40 mg/kg cocaine while in the home cage. Twenty-four hours later, the Unpaired mice were injected with saline (Unpaired-vehicle); one Paired group was injected with saline (Paired-vehicle); a second Paired group was injected with 5 mg/kg DMTU (Paired-5 mg/kg DMTU); and a third Paired group was injected with 10 mg/kg DMTU (Paired-10 mg/kg DMTU). Thirty minutes after the injections, all mice were injected with saline and then placed in the testing chamber and given 30 minutes to explore freely. Locomotion was monitored using the Digi scan photocell apparatus and recorded as horizontal activity (counts).

A conditioned effect of cocaine would be inferred if Paired mice were significantly more active than Unpaired controls. The effect of DMTU on expression of the conditioned cocaine response was examined by comparing locomotor activity of the Paired-vehicle group with the DMTU groups (Paired-5 mg/kg DMTU and Paired-10 mg/kg DMTU).

Data Analysis. Activity was measured by the number of photobeam breaks during the 30-min locomotor test and then represented as horizontal activity (counts). Preliminary findings indicated that the most significant modulation of cocaine-conditioned responding could be observed during the final 15 minutes of the test session. Consequently, the average horizontal activity from the last 15 minutes for each mouse was analyzed in a one-way analysis of variance (ANOVA) with treatment group as the factor. Planned comparisons were made through the use of single degree-of-freedom F tests in which the denominator was the error for the overall analysis. The alpha level was set at 0.05 for all analyses.

B. Results

DMTU blocks cocaine-conditioned locomotion. In one series of experiments, DMTU was found to block expression of a conditioned locomotor stimulant effect of cocaine. The conditioning of the cocaine stimulation is an experimental model of the abnormal synaptic plasticity elicited by cocaine exposure in a salient novel environment.

Figure 2:
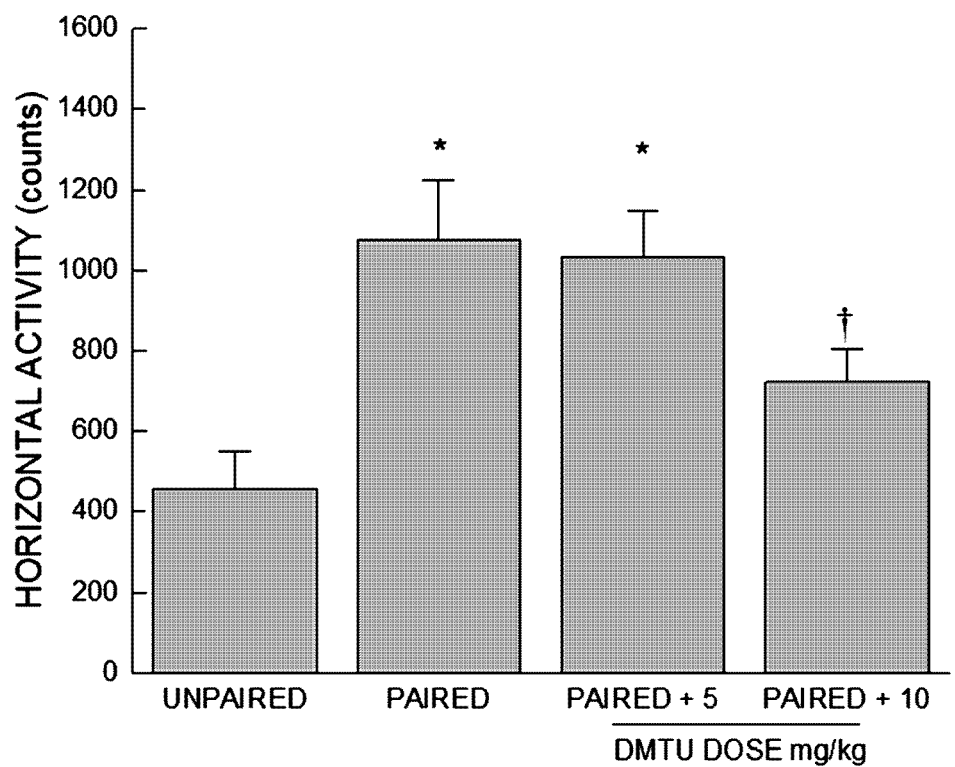
FIG. 2. Locomotor activity during expression test when mice were administered either vehicle (Unpaired-vehicle or Paired-vehicle) or DMTU (Paired-5 mg/kg or Paired-10 mg/kg). Enhanced activity was observed in mice that had previously experienced cocaine paired with the chamber (Paired-vehicle and Paired-5 mg/kg DMTU) compared with mice that experienced cocaine in the home cage (Unpaired-vehicle). A DMTU dose of 10 mg/kg administered to a paired group prior to the expression test attenuated expression of the cocaine-conditioned locomotor response. Each bar represents average horizontal activity (counts)+S.E. for the last 15 minutes of the expression test for the different experimental groups: Unpaired-vehicle, Paired-vehicle, Paired-5 mg/kg DMTU, Paired-10 mg/kg DMTU (n=8/experimental group). * represents significant difference from the Unpaired-vehicle group, and † represents significant difference from the Paired-vehicle group, $p<0.05$.

Data from the expression test are shown in FIG. 2. Mice that had been previously exposed to cocaine in the test chamber (Paired-vehicle and Paired-5 mg/kg DMTU) were significantly more active than mice that had experienced cocaine in their home cages (Unpaired-vehicle), confirming that a cocaine-conditioned response was present. Administration of 10 mg/kg DMTU (Paired-10 mg/kg DMTU) prior to expression testing significantly inhibited cocaine-conditioned locomotor activity, whereas the lower dose of DMTU (Paired-5 mg/kg DMTU) did not affect activity.

These observations were supported by one-way analysis of variance (ANOVA) that revealed a significant effect of experimental group, $F (3, 28)=6.70$, $p<0.002$. Planned individual comparisons using single degree-of-freedom F tests indicated that horizontal activity counts were significantly higher in the Paired-vehicle and Paired-5 mg/kg DMTU groups than in the Unpaired-vehicle group. DMTU modulated this cocaine-conditioned responding, as demonstrated by the significant reduction in activity counts of the Paired-10 mg/kg DMTU when compared with the Paired-vehicle group (all $ps<0.035$).

DMTU selectively blocks cocaine-induced conditioned place preference in a high drug-seeking subset. This study confirmed previous suggestions for DMTU using a model of drug-enhanced memory based on preference rather than motor activity. Additionally, this testing allowed selection of a subpopulation of high cocaine-seeking mice that is hypothesized to model high addiction and relapse risk.

Cocaine hydrochloride and N, N'-dimethylthiourea were obtained from Sigma-Aldrich (St. Louis, Mo.). All compounds were dissolved in 0.9% saline and administered intraperitoneally (i.p.). All mice underwent standard place conditioning. As depicted in FIG. 3, the procedures of the first four days were identical to those described previously (Shetty et al., 2017). A preference score was calculated for each individual mouse using the following equation: Time spent on S+ (at test)−Time spent on S+ (at pretest). The preference score assesses the nature and magnitude of drug conditioning to the S+ floor, with positive numbers reflecting an increase in preference for S+ following the experience with cocaine and negative numbers indicating a decrease in preference following experience with cocaine. A second test session was conducted 24 hours later (on day 5). This test was identical to the test session on day 4 except that 30 minutes prior to testing, mice were pretreated with either 5 or 10 mg/kg DMTU (i.p.). A preference score was calculated after the second test in a similar fashion as described for the first preference test. A significant change in preference score on the second test relative to the first would indicate that DMTU had a modulating effect on cocaine-conditioned place preference.

Data Analysis. Following two pairings of 15 mg/kg of cocaine with S+, data from Test 1 indicated that most, but not all mice increased their preference for S+. The existence of subgroups was determined through application of K-means clustering analysis (SYSTAT v. 13.1). In this fashion, Test 1 data was partitioned into 3 subgroups: mice with high positive preference scores (labeled as High Seeker group), mice with low positive preference scores (labeled as Low Seeker group), and mice with negative preference scores (labeled as Avoider group).

Data from the mice treated with 5 mg/kg DMTU during Test 2 were analyzed separately from data from mice treated with 10 mg/kg DMTU. Separate one-way repeated measures analysis of variance (ANOVA) was conducted, with test (comparison of preference score on test day 1 and day 2) as a within-subject factor.

To assess the ability of DMTU (by either the 5 mg/kg or 10 mg/kg dose) to reduce cocaine-induced preference on different subsets of mice, within-subject planned comparisons of preference scores on test 1 and 2 were performed for each cluster separately (Avoider, Low Seeker, High Seeker). Alpha was set to 0.05.

Following conditioning with 15 mg/kg of cocaine, significant place preference was observed on Test 1, in groups of mice subsequently treated with either 5 mg/kg (see FIG. 4, panel A) or 10 mg/kg of DMTU (panel B), $p<0.001$. However, on Test 2, conditioned preference was not significantly altered by pretreatment with either 5 mg/kg or 10 mg/kg of DMTU (when clusters were combined, $p>0.192$). Subsequently, when mice were divided into three cluster groups (Avoiders, Low Seekers, High Seekers), the outcome of cocaine-conditioned place preference by DMTU was considerably different. When only the High Seeker subset was considered, both 5 mg/kg and 10 mg/kg of DMTU administered prior to Test 2 significantly reduced preference scores, $p<0.026$. Neither dose of DMTU succeeded in blocking preference scores of the Avoider group or the Low Seeker group.

Separate two-way repeated measures analysis of variance for each of the doses of DMTU, with Clusters and Test (preference score test 1 and test 2) as factors, indicated a significant interaction of Cluster with Test ($p<0.014$). Furthermore, planned comparisons of preference scores on test 1 and 2 for each of the clusters (Avoiders=1, Low Seekers=2, High Seekers=3) for attenuation by either 5 mg or 10 mg of DMTU, indicated a significant difference between the preference scores for cluster 3 ($p<0.026$ denoted on Figure-2 with *) but not for cluster 1 or 2.

These findings support the potential application of DMTU in the treatment of psychostimulant addiction and relapse, by virtue of an ability to block expression of the abnormally strong memories associated with psychostimulant use. That expression of cocaine-conditioned behavior may be diminished by a redox-modulating compound such as DMTU confers significant advantages over existing therapeutic approaches that target monoamine neurotransmitters involved directly in drug and natural rewards.

Example 2

Cocaine-Conditioned Locomotion

A. Materials and Methods

Subjects. Male Swiss-Webster mice (Hsd:ND4) were obtained from Harlan Laboratories. Mice were group-housed on a 12-h/12-h light/dark cycle, with access to food and water ad libitum. Mice were tested at approximately 8 weeks of age during the light portion of the cycle. All housing and procedures were in accordance with the guidelines of the Guide for Care and Use of Laboratory Animals (Institute of Laboratory Animal Resources, 2011) and were approved by the University of North Texas Health Science Center Animal Care and Use Committee.

Test Compounds. (−)-Cocaine HCl (40 mg/kg) was obtained from the National Institute on Drug Abuse. N-acetylcysteine (10-250 mg/kg), dimethylthiourea (5-50 mg/kg), and (+)-alpha-tocopherol (25-100 mg/kg) were obtained from Sigma-Aldrich (St. Louis, Mo.), L-ascorbic acid (25-500 mg/kg) was obtained from Mallinckrodt Chemicals (Phillipsburg, N.J.), and apocynin (1-50 mg/kg) was obtained from Tocris Bioscience (Minneapolis, Minn.). All compounds were administered intraperitoneally (i.p.). Cocaine, N-acetylcysteine, dimethylthiourea, and apocynin were dissolved in 0.9% saline vehicle, L-ascorbic acid was dissolved in 0.9% saline and 10 N NaOH, and alpha-tocopherol was suspended in 2% methylcellulose. Test compounds were chosen for their ability to alter redox state and were administered prior to placement into the activity chamber on the test day.

Conditioning and Testing Procedures. Prior to all testing sessions, mice were weighed and labeled according to their treatment. The locomotor activity of mice was measured using the Digiscan apparatus (Omnitech Electronics, Columbus, Ohio) and digital tracking software. Individual mice were placed into a clear acrylic chamber (40.5×40.5× 30.5 cm), that was in turn placed inside a metal frame (49×53×9 cm) lined with photobeam cells. The acrylic chamber and metal frame were enclosed within a sound suppressing cabinet (99.0×49.50×51 cm) lined with sheets of insulation and a fan for ambient noise. While in the chamber, the photobeams were interrupted by the mouse's activity, which was then recorded by the computer. This activity was categorized into basic components, including horizontal activity (counts) and horizontal distance travelled (cm) as measured by photobeam breaks. A single injection of cocaine (40 mg/kg, i.p.) was administered to different groups of Swiss-Webster mice via intraperitoneal injection (i.p.), in either a locomotor activity testing apparatus or the home cage, 2 hours following an activity test under saline. Animals given cocaine within the testing apparatus were designated "paired"; whereas, animals given cocaine within the home cage were designated "unpaired". Mice placed in the testing chambers were given 30 minutes to explore freely and locomotion were monitored using the Digiscan photocell apparatus. A conditioned effect of cocaine was inferred by an increase in horizontal activity relative to home cage cocaine controls during a test in the same apparatus on the following day.

Data Analysis. The behavioral data was scored according to the amount of activity during each locomotor test, as measured by photobeam breaks and represented as horizontal activity (counts) using 5 minute time bins across 30 minutes. Results were expressed as mean±S.E. and presented as compared to values obtained from paired and unpaired groups. Based upon preliminary findings indicating that the most significant modulation of cocaine-conditioning could be observed during final 15 minutes of the test session, data from the last 3 time bins were averaged and analyzed using one-way analysis of variance with Treatment as a factor. Individual comparisons of treatment vs. control groups were performed using single degree of freedom tests. Effects of redox modulating compounds on cocaine-conditioned responses were inferred using data representing an increase or decrease in locomotor activity on acquisition and expression challenge days. A median effective dose (ED50) from preliminary locomotor activity data and a median antagonism dose (AD50) from acquisition/expression test data were calculated with linear regression analysis using Origin Pro graphing utility. Selectivity of the test compound for modulation of the conditioned effect versus acute hypokinetic action was inferred using an ED50:AD50 ratio.

B. Results

Cocaine-conditioned locomotion is altered by redox state modulating compounds. As shown in FIG. 5a, there was no significant main effect of NAC on acute cocaine-induced hyperlocomotion [$F(5,41)=2.195$, $p=0.073$]. As shown in FIG. 5b, there was no significant main effect of NAC treatment [$F(5,57)=1.209$, $p=0.317$] on acquisition, although post-hoc analyses showed that NAC (250 mg/kg) significantly attenuated acquisition of the conditioned locomotor response represented by the paired control group [$p=0.037$]. FIG. 5c depicts a main effect of NAC treatment [$F(3,28)=6.065$, $p=0.003$] on expression of the conditioned response, with post-hoc analyses showing a significant attenuation by NAC (100 mg/kg). As shown in FIG. 6a, there was no significant main effect of DMTU treatment of acute cocaine-induced hyperlocomotion [$F(4,35)=1.455$, $p=0.237$]. Analysis of the data showed a significant main effect of dimethylthiourea treatment on acquisition of the cocaine-conditioned locomotor response [$F(4,35)=6.471$, $p=0.001$], and post-hoc analyses showed that DMTU (50 mg/kg) significantly attenuated acquisition [$p<0.001$]. DMTU treatment also had a significant effect on expression of the conditioned response [$F(4,35)=6.384$, $p=0,001$], and post-hoc analyses showed DMTU (25-50 mg/kg) significantly attenuating expression.

As shown in FIG. 7a, Vitamin C (100 mg/kg) facilitated the acute hyperkinetic effect of cocaine [$F(5,58)=3.262$, $p=0.012$], though failed to attenuate acquisition [$F(5,42)=0.853$, $p=0.52$] and expression [$F(5,42)=0.303$, [$=0.909$] of the cocaine-conditioned locomotor response, as depicted in FIGS. 7b and 7c. Though, post-hoc analysis showed that 100 mg/kg vitamin C facilitated acquisition of the conditioned locomotor response, during the initial 15 min of the test. FIG. 8a shows that Vitamin E had no effect on the acute effect of cocaine [$F(5,42)=1.235$, $p=0.31$], and in tests for conditioned response, vitamin E failed to attenuate acquisition [$F(5,41)=0.199$, $p=0.961$] and expression [$F(3,27)=1.254$, $p=0.31$] of the conditioned locomotor response, as depicted in FIGS. 8b and 8c. There was no significant main effect of apocynin treatment on acute cocaine-induced hyperlocomotion [$F(6,49)=0.913$, $p=0.493$]; however, post hoc analysis did show that 25 mg/kg apocynin facilitated expression of the conditioned response during the initial 15 min of the test. Apocynin had no effect on acquisition [$F(6,49)=1.668$, $p=0.149$] and no effect on expression [$F(5,42)=1.784$, $p=0.137$] of the cocaine-conditioned locomotor response, as depicted in FIGS. 9b and 9c.

Example 3

DMTU Blocks Nicotine Induced Locomotion

A. Materials and Methods

Animals. Male Swiss.Webster mice (Hsd: ND4) were obtained from Envigo Laboratories. Mice were group-housed on a 12-h/12-h light/dark cycle, with access to food and water ad libitum. Mice were tested at approximately 8 weeks of age during the light portion of the cycle. All housing and procedures were in accordance with the guidelines of the Guide for Care and Use of Laboratory Animals (Institute of Laboratory Animal Resources, 1996) and were approved by the University of North Texas Health Science Center Animal Care and Use Committee.

Test Compounds. (−)-Nicotine tartrate (1.6 mg/kg) was obtained from Cayman Chemical (Ann Arbor, Mich.), N, N'-dimethylthiourea (DMTU) (5 and 10 mg/kg) was obtained from Sigma-Aldrich (St. Louis, Mo.). Chantix (varencline, 3 mg/kg) was obtained from National Institute on Drug Abuse. All drugs were dissolved in 0.9% saline and pH was maintained at 7.

Testing Procedures. Prior to all testing sessions, mice were weighed and labeled according to their treatment. The locomotor activity of mice was measured using the Digiscan apparatus (Omnitech Electronics, Columbus, Ohio) and digital tracking software. Individual mice were placed into a clear acrylic chamber (40.5×40.5×30.5 cm) that was contained inside a metal frame (49×53×9 cm) lined with photobeam cells. The acrylic chamber and metal frame were enclosed within a sound-suppressing wood cabinet (99.0× 49.5×51.0 cm) lined with sheets of insulation and a fan for ambient noise. The photobeams were interrupted by the mouse's activity within the chamber, which was then recorded by the computer. Activity was categorized into basic components which included horizontal activity (counts). In all studies, horizontal activity (interruption of photocell beams) was measured for 120 min within 10-min periods.

Figure 10:
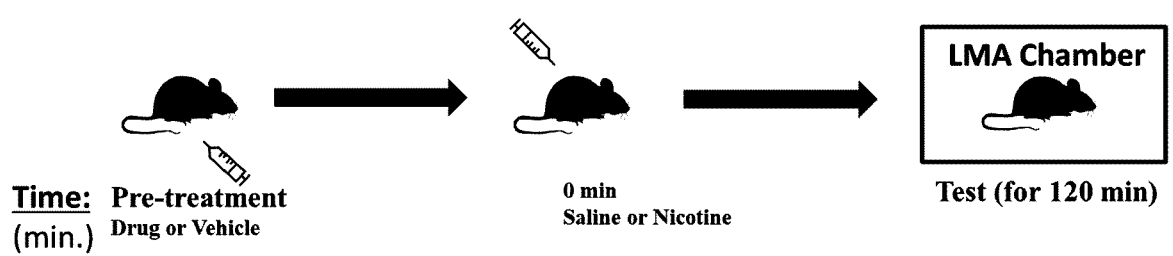
FIG. 10. Locomotor activity timeline.

Different groups of Swiss-Webster mice were pretreated via injection (IP) with either DMTU (5 or 10 mg/kg), or Chantix (varenicline, 3 mg/kg) or vehicle (0.9% saline) for 30 minutes (FIG. 10). Following pretreatment all groups were mice were injected via the subcutaneous (sc) route with either 0.9% saline or r nicotine (1.6 mg/kg) just prior to placement in the activity chamber. The activity of all mice were recorded for a period of 2-h (FIG. 10). Locomotion was monitored using the Digiscan photocell apparatus and recorded as horizontal activity (counts).

Data Analysis. Activity was measured by the number of photobeam breaks during the 2-h locomotor test and then represented as horizontal activity (counts). Preliminary findings indicated that nicotine has a depressant effect on mice during the 1-h and a stimulant effect in the second hour. Data presented in the graphs indicates the average horizontal activity from 60-90 min for each mouse was analyzed in a one-way analysis of variance (ANOVA) with treatment group as the factor. Planned comparisons were made through the use of single degree-of-freedom F tests. The alpha level was set at 0.05 for all analyses.

B. Results

DMTU blocks nicotine induced locomotion. Nicotine at the dose of 1.8 mg/kg has a biphasic action, acting as depressant in the first hour and a stimulant in the second hour. In a series of experiments, Chantix (3 mg/kg) and DMTU (5, 10 mg/kg) was found to block locomotor stimulant effect of nicotine.

These observations were supported by separate one-way analyses of variance (ANOVA) for each treatment (A, B, C) that revealed a significant effect of experimental group, F's $(3, 60) > 4.50$, p's$<0.007$. Planned individual comparisons using single degree-of-freedom F tests indicated that horizontal activity counts were significantly increased in the nicotine alone group. Both doses of DMTU modulated nicotine induced stimulant action, however only pretreatment with 10 mg/kg DMTU significantly reduced the nicotine stimulant activity (counts) when compared with the nicotine alone group (FIGS. 11A and 11B). Groups of mice pretreated with Chantix (3 mg/kg) either alone or with nicotine indicated a significant reduction their motor activity (FIG. 11C) (all ps$<0.005$), whereas DMTU alone failed to alter the motor activity of mice (all ps$>0.005$).

The locomotor activity test against 1.8 mg/kg nicotine shows a sensitivity to the standard of varenicline (Chantix), suggesting a predictive validity of this test for clinical application. Under these assumptions, the suggestion of the dataset is that DMTU may be an effective drug for smoking cessation that has fewer side effects when compared with varenicline. This conclusion is based on its ability to selectively diminish the locomotor stimulant effect of nicotine, without itself producing a depressant effect on locomotor activity.

The invention claimed is:

1. A method of treating or preventing an addictive behavior in a subject, the method comprising administering to said subject a composition comprising an effective amount of N,N'dimethylthiourea (DMTU).

2. The method according to claim 1, wherein the addictive behavior is exhibited by the subject following exposure of the subject to at least one stimulus, the stimulus inducing the addictive behavior.

3. The method of claim 2, where in the stimulus is alcohol, caffeine, nicotine, *cannabis*, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine and methylamphetamine.

4. The method of claim 1, wherein DMTU is administered at 1 to 100 mg/kg.

5. The method of claim 1, wherein the DMTU is administered orally, intratracheally, intravenously, intramuscularly, intraperitoneally, percutaneously, topically, or subcutaneously.

6. The method of claim 1, wherein a subject is administered DMTU on a regular schedule.

7. The method of claim 1, wherein the subject is administered DMTU daily.

8. A method for mitigating relapse into addiction of a subject, the method comprising administering to said subject a composition comprising an effective amount of N,N'dimethylthiourea (DMTU).

9. The method of claim 8, wherein DMTU is administered at 1 to 100 mg/kg.

10. The method of claim 8, wherein the DMTU is administered orally, intratracheally, intravenously, intramuscularly, intraperitoneally, percutaneously, topically, or subcutaneously.

11. The method of claim 8, wherein a subject is administered DMTU on a regular schedule.

12. The method of claim 8, wherein the subject is administered DMTU daily.

13. A method for reducing the addictive effect of re-exposure or continuous exposure to at least one agent, behavior, or stimulus which induces addictive behavior in a subject, wherein the subject is an addict or having a risk of developing addiction, the method comprising administering to said subject a composition comprising an effective amount of N,N'dimethylthiourea (DMTU).

14. The method of claim 13, wherein DMTU is administered at 1 to 100 mg/kg.

15. The method of claim 13, wherein the DMTU is administered orally, intratracheally, intravenously, intramuscularly, intraperitoneally, percutaneously, topically, or subcutaneously.

16. The method of claim 13, wherein a subject is administered DMTU on a regular schedule.

17. The method of claim 13, wherein the subject is administered DMTU daily.

18. A method of treating or preventing or suppressing relapse to addiction, relapse use of an addictive agent or practice of an addictive or compulsive behavior in a subject, the method comprising administering to said subject a composition comprising an effective amount of N,N'dimethylthiourea (DMTU).

19. The method of claim 18, wherein DMTU is administered at 1 to 100 mg/kg.

20. The method of claim 18, wherein the DMTU is administered orally, intratracheally, intravenously, intramuscularly, intraperitoneally, percutaneously, topically, or subcutaneously.

21. The method of claim 18, wherein a subject is administered DMTU on a regular schedule.

22. The method of claim 18, wherein the subject is administered DMTU daily.

\* \* \* \* \*